United States Patent [19]

Erb

[11] Patent Number: 4,690,677
[45] Date of Patent: Sep. 1, 1987

[54] URINE COLLECTION SYSTEM FOR FEMALES

[75] Inventor: Robert A. Erb, Valley Forge, Pa.

[73] Assignee: Daltex Medical Sciences, Inc., West Orange, N.J.

[21] Appl. No.: 780,056

[22] Filed: Sep. 25, 1985

[51] Int. Cl.⁴ .......................................... A61M 25/00
[52] U.S. Cl. .................................... 604/329; 604/327
[58] Field of Search ............................. 604/327–332, 604/336–338, 164, 170, 329

[56] References Cited

U.S. PATENT DOCUMENTS

| | | | |
|---|---|---|---|
| 3,556,102 | 1/1971 | Davis | 604/329 |
| 3,886,933 | 6/1975 | Mori et al. | 128/348.1 |
| 4,246,901 | 1/1981 | Michaud | 604/329 |
| 4,284,081 | 8/1981 | Kasper et al. | 604/170 |
| 4,563,183 | 1/1986 | Barrodale | 604/329 |
| 4,571,239 | 2/1986 | Heyman | 604/170 |

FOREIGN PATENT DOCUMENTS

| | | | |
|---|---|---|---|
| 1004104 | 1/1977 | Canada | 604/329 |
| 2416036 | 4/1975 | Fed. Rep. of Germany | 604/329 |
| 2817571 | 10/1978 | Fed. Rep. of Germany | 604/329 |
| 2070936 | 9/1981 | United Kingdom | 604/329 |

Primary Examiner—Stephen C. Pellegrino
Assistant Examiner—John Ferros
Attorney, Agent, or Firm—Lieberman, Rudolph & Nowak

[57] ABSTRACT

A urine collection system for females comprised of a soft, flexible, sealing member forming a seal around the external urethral ostium, by conformation to and adhesion to the tissue surface. A conduit, or drain, passes through the sealing member leading to collection and storage means for the urine. A positioning or orientation member is provided to achieve alignment of the conduit lumen through the sealing member with the urethral orifice.

25 Claims, 9 Drawing Figures

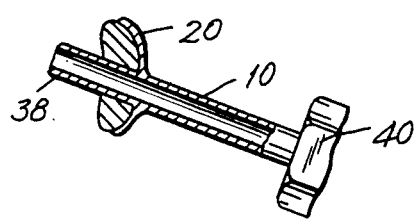 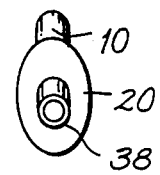
FIG. 4   FIG. 4a
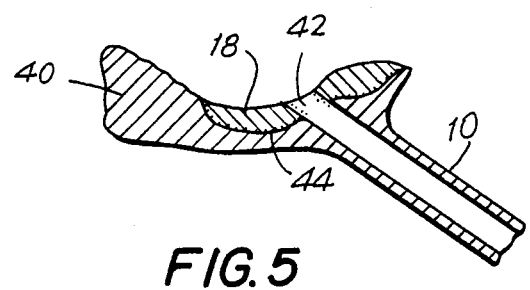
FIG. 5
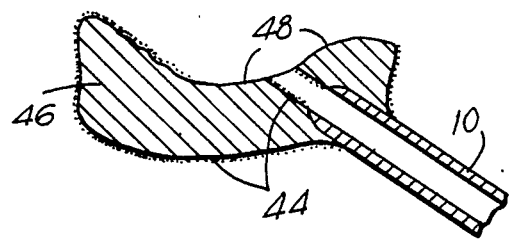
FIG. 6

URINE COLLECTION SYSTEM FOR FEMALES

FIELD OF THE INVENTION

This invention relates in general to a urine collection system for females. In a further aspect, this invention is directed to a urine collection device particularly useful as an alternate system for long term in-dwelling urinary cathethers whereby urinary tract infection is minimized. A further aspect of this invention is directed to a urinary collection system, which can be utilized in any orientation of the body with respect to gravity and even under weightless conditions, such as those encountered in a gravity-free environment.

DESCRIPTION OF THE PRIOR ART

The urinary catheter is one of the most useful of medical prosthetic devices and is employed widely for urine output measurement, bladder outlet obstruction and for the management of incontinence. Hygienic management of urinary incontinence and of the inability to use conventional toilet facilities because of some physical handicap is a serious problem and particularly so for women. In many cases incontinent women are often reduced to wearing diaper-type garments containing absorbent materials. For certain classes of non-ambulatory patients in hospitals and nursing homes, catheterization is widely utilized for the collection of urine.

However, it is well known that chronic catheterization often leads to urinary tract infection. In acute care hospitals, the majority of patients have the urinary catheter in place for a relatively short period of time, such as from two to four days. In those patients which are catheterized for longer periods, an unusually large number become bacteriuric. Although it has been reported that only one to two percent of bacteriuric catheterized patients will develop bacteremia, due to the large number of patients that are catheterized, the incident of bacteremia is unduly high. It is known that the urinary tract is the most common source of gram-negative rod bacteremia in patients confined to hospitals. It has also been confirmed by clinical observation that patients with a catheter in place for 30 days or more have a 78-95% chance of developing bacteremia. In fact, it has been reported in the literature that the insertion of a uretheral catheter causes bacteremia in about 8% of those being catheterized. Once the catheter is in place, the patient has a 5-10% daily risk of developing bacteremia. Accordingly, as indicated above, although only 1-2% of bacteriuric patients will develop symptomatic gram negative rod bacteremia, the number of catheterized patients is so large that the catheterized urinary tract is the most frequent source of nosocomial gram-negative rod bacteremia in the United States. Hence, a device which would minimize or eliminate the incidents of urinary tract infection and yet provide a simple and safe method for the collection of urine, particularly for females, would be of great benefit to the health care and medical profession.

The patent literature discloses numerous inventions pertaining to the collection of urine. For example, U.S. Pat. No. 3,335,714, which issued Aug. 15, 1967, discloses and claims an apparatus for obtaining urine samples from female patients where special problems are introduced in obtaining urine samples free from extra urethral contamination. Because of the positioning of the urethra, difficulties have been encountered in obtaining truly representative urine samples from females. Usually such samples are obtained by inserting a catheter into the urethra, with urine then following directly from the bladder. This procedure, however, has the potential danger of introducing bacteria into what previously was a sterile bladder and hence renders the patient susceptible to urinary tract infection. Although the device of this patent avoids the use of a catheter, it is merely used for the collection of urine samples and hence not designed for wearing for any extended period of time.

In U.S. Pat. No. 4,194,508, which issued Mar. 25, 1980, there is disclosed an externally applied urinary collection device for incontinent females. The device disclosed in this patent has a flexible cop like diaphram to fit over the urethral opening to direct urine to a collection receptacle without leakage. For ambulatory females, the device can contain a vaginal insert for further stabilization and support while the device is in position.

A urine collection device for women is also disclosed in U.S. Pat. No. 4,198,979, which issued Apr. 22, 1980. This device is comprised of a generally funnel shaped rigid collection means having a flanged wide orifice, with an upper surface containing an adhesive and wherein the flanged wide orifice is shaped to fit within the contours of the perminimum cavity. It is indicated in the patent that the whole orifice can cover both the urethral and vaginal orifices to collect discharges therefrom.

A further female incontinence device is described in U.S. Pat. No. 4,421,511, which issued Dec. 20, 1983. In the device disclosed therein, an external resilient pad makes sealing engagement with the persons's anatomy that is external to the labia majora and a funnel having a rim dimensioned to engage that portion of the anatomy immediately surrounding the urethra.

In U.S. Pat. No. 4,457,314, which issued July 3, 1984, an additional female urine collection device is disclosed which is comprised of a cup shaped receiving chamber provided with a flexible lift on the periphery thereof for sealing around the urethral orifice. A flexible duct leads to a compressible collection reservoir and a two-way anti-backflow mechanism is also provided.

Although each of the above patents discloses collection systems for use by females, without the need for catheterization, each is not without its disadvantages. For example, many of the devices disclosed in the prior art do not form a tight seal with the anatomy of the user and hence are susceptible to leaking of urine from the collection device. This is a particular disadvantage for ambulatory females and those engaged in even moderate physical activity. Moreover, certain of the devices disclosed are merely used for the collection of urine samples and were never intended for prolonged use, such as an incontinent person might require. It has also been noted that the devices disclosed in the patent literature, which avoid the use of a catheter, are comprised of collection devices which are much larger in diameter than the uretheral orifice and accordingly tend to entrain or entrap air making disposal difficult. This is particularly critical if the user is horizontally positioned, or if the urine collection device were to be employed in a gravity free environment such as outer space applications. Moreover, the failure of the known devices to align themselves properly with the uretheral orifice often results in leakage, entrapment of air and other undesirable features. The urine collection of the present invention overcomes the disadvantages noted for systems which employ catheterization, as well as the devices discussed above for the collection of urine from females.

Accordingly, one or more of the following objects will be achieved by the practice of the present invention.

It is an object of the present invention to provide a urine collection system, or device, for females. A further object is to provide a urine collection device which is particularly useful as an alternate system to long term in-dwelling urinary catheters. Another object of the present invention is to provide a urinary collection system which can be utilized under weightless conditions. Another object of the present invention is to provide a urine collection system which can function when the user is in a horizontal position. A further object is to provide a urine collection system which can be simply applied, used, and removed in a confined space without toilet facilities, such as in private aircraft, submersibles, automobiles and guard stations. A still further object of the present invention is to provide a urine collection system for incontinent females whether confined to a hospital or nursing home, or ambulatory and physically active in their daily living. Another object of the present invention is to provide a collection system which is capable of use for a short term or extended periods of time and which minimize the incidence of urinary tract infection. Another object is to provide a urine collection system which avoids the insertion of a catheter into the urethral orifice. Another object of the present invention is to provide a system for the collection of urine wherein the exit drain has a small diameter approximately equal to the diameter of the urethral orifice. A still further object is to provide a system wherein the exit drain is attached to the urethral opening in such a manner that the drain need not penetrate the urethral orifice. A further object of the present invention is to provide a urine collection system wherein the exit drain is attached at the urethral orifice by means of a flexible adhesive seal. These and other objects will readily become apparent to those skilled in the art in light of the teachings herein set forth.

SUMMARY OF THE INVENTION

In its broad aspect, the present invention is directed to a urine collection system for females which is comprised of a soft, flexible, sealing member forming a seal around the external urethral ostium, by conformation to and adhesion to the tissue surface; a conduit, or drain, through the sealing member leading to collection and storage means for the urine; and a positioning or orientation member to provide alignment of the conduit lumen through the sealing member with the urethral orifice.

BRIEF DESCRIPTION OF THE DRAWINGS

The urine collection device of the present invention will be more readily understood by reference to the drawings, wherein:

FIG. 4 is a cross-sectional view of a nonretracting urethral positioning member of the urine collection system of the present invention.

FIG. 4a is an end view of the urethral positioning member of FIG. 4.

FIG. 5 is a cross-sectional view of the urine collection device with a vaginal orientation member.

FIG. 6 is a cross-sectional view of the urine collection device wherein the sealing medium makes up the bulk of the orientation member.

DETAILED DESCRIPTION OF THE DRAWINGS & INVENTION

Figure 1:
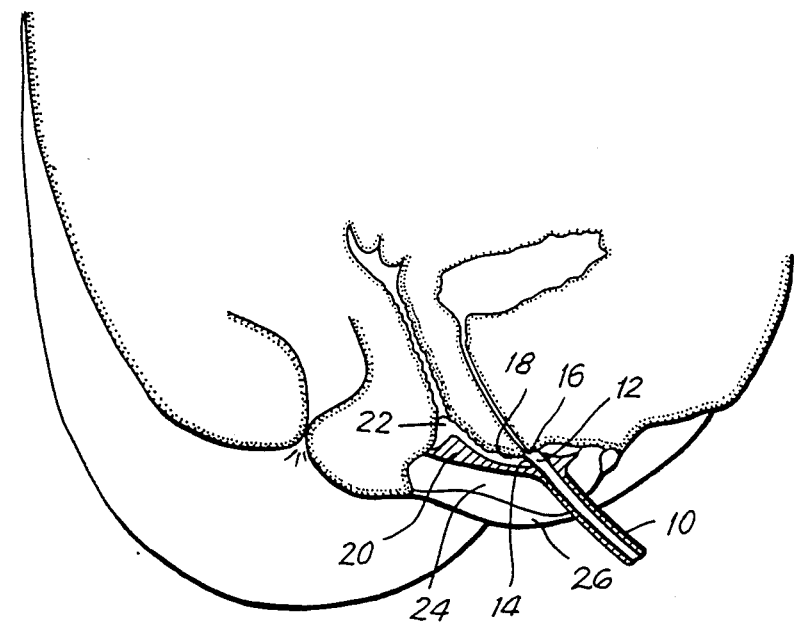
FIG. 1 is a sagittal section through the female pelvis showing the urine collection system of the present invention, wherein the drain tube is sealably adhered around the urethral ostium.

With further reference to the drawings, FIG. 1 is a sagittal section through the female pelvis area showing a portion of the urine collection system of the present invention and comprised of flexible conduit 10, having the lumen 12 of its first end 14, positioned in communication with urethral ostium 16, and held in juxtaposition with the ostium by sealing medium 18, which is disposed in support member 20. Also depicted in FIG. 1 is a further embodiment of the present invention, wherein the support member 20 is so configured as to serve as an orientation member for maintaining the conduit 10 and lumen 12 in fixed relationship to the urethral ostium 16 by having a portion of said member fitted into the vaginal ostium 22 and further held in place by the labia minora 24 and labia majora 26.

Figure 2:
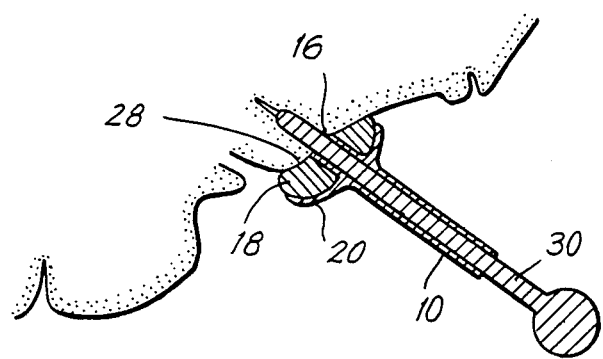
FIG. 2 is a sagittal section through the female pelvis depicting a urethral alignment member in the placement mode for attachment of the urine collection system.

FIG. 2 is another sagittal section taken through the female pelvis area and depicts one embodiment of the present invention, wherein a removable orientation member 30 is employed to align the conduit 10, with urethral ostium 16, while attchment of the urine collection system is made to the tissue surrounding the urethral ostium with the sealing medium 18 contained in support member 20. The orientation member 30 consists of a rounded-end rod, preferably of a low friction material, such as polytetrafluorine polymer, or other inert material which can be lubricated, if desired, for easy insertion. In marked contrast to a urethral catheter, the orientation member is not inserted the full length of the urethra (which is about 40 mm), but only a sufficient distance to insure proper alignment of the flow channel of conduit 10 and the urethral ostium, a distance of about 9 mm at most. The use of a short insertion length and the limited time that orientation member 30 is inserted into the urethra greatly minimizes any potential for infection.

After proper alignment of conduit 10, with the ostium 16, slight pressure on support member 20 towards the body of the user insures proper adhesion of sealing medium 18 to the body tissue 28.

Figure 2A:
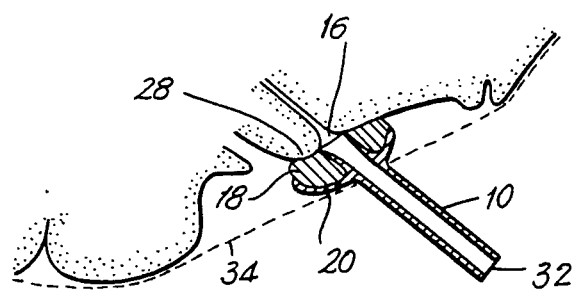
FIG. 2a is a sagittal section showing the urine collection system affixed to the female anatomy in the use mode.

Thereafter, while pressure is maintained on the support member 20 to hold it in place, orientation member 30 is withdrawn from conduit 10 leaving a leak-free, continuous channel, as depicted in FIG. 2a, extending from the urethral ostium through the conduit 10 to a collection and storage zone, not shown. End 32 of conduit 10 can be fitted with quick-connect fittings, not shown, for attachment to the remainder of the system. Optional garment, shown as dotted line 34, and worn by the user, can also aid in maintaining the system in place.

Figure 3:
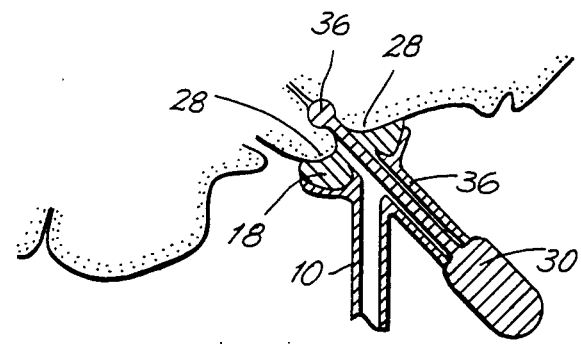
FIG. 3 is a sagittal section showing another embodiment of the present invention and the alignment member positioned in the placement mode for affixing the urine collection system.
Figure 3A:
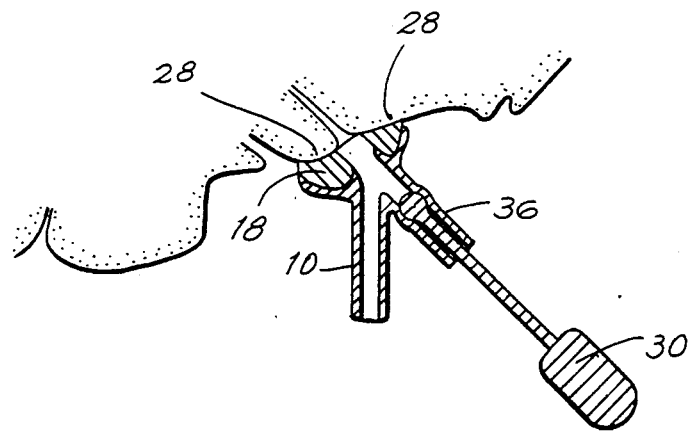
FIG. 3a is a section through the female pelvis showing the alignment member in its retracted position and the urine collection device in the use mode.

FIG. 3 depicts a further embodiment of the present invention and is also a sagittal section through the female pelvis area showing a portion of a urine collection of the present invention, wherein the orientation member is not removable and is an integral part of the apparatus. In FIG. 3 and FIG. 3a, the orientation member 30 is shown respectively, in the placement mode, and in the use mode. In the placement mode, conduit 10 of the urine collection system is aligned with the urethral ostium and stem end 36 of orientation member 30 inserted into the ostium. While in proper alignment, the system is adhesively affixed to the body tissue 28 by means of sealing medium 18 and slight pressure on support member 20.

As depicted in FIG. 3 and FIG. 3a, conduit 10 and support member 20 are fitted with a side conduit 36 through which orientation member 39 can slidably move from the placement mode to a position which does not interfere with the flow of urine. Side conduit 36 forms a leak-proof seal with orientation member 30.

FIG. 4 is a cross-sectional view of a further embodiment of the present invention and shows orientation member 38 which is an integral and permanent part of conduit 10 and support means 20. In this instance, the orientation member 38 is retained in place during use. However, as opposed to a urethral catheter, the orientation member 38 only invades the urethra a small distance, usually less than 10 millimeters and accordingly, the potential for infection is kept at a minimum. This type of device is particularly well suited when a urine collection system is required for relatively short periods of time, such as a few days. While it can also be utilized for longer periods of time, it is preferred in those instances to employ the system, as hereinbefore described, wherein the conduit 10 does not invade the urethra, but is merely sealably fixed to the body of the urethral ostium.

The embodiment of the invention depicted in FIG. 4 shows a portion of a quick-connect coupling 40 attached to conduit 10 and which leads to a urine collection and storage zone, not shown.

FIG. 4a is an end view of the orientation member 38, support member 20 and conduit 10, wherein all form an integral and permanent part of the system. As previously indicated, the internal diameter of orientation member 38 and conduit 10 are essentially the same as that of the urethra.

FIG. 5 is a cross-sectional view of a portion of the urine collection system of the present invention and shows positioning member 40 which can fit into the vaginal ostium and forms an integral part of conduit 10. Member 40 has contained on a portion of its surface, adjacent to the conduit opening 42, sealing medium 18 for affixing the system to the tissue surrounding urethral ostium. Positioning member 40 can be fabricated from a semi-rigid, yet flexible polymeric material, as hereinbefore defined, and can contain a thin layer of material 44 between member 40 and sealing member 18.

FIG. 6 is another cross-sectional view of a portion of the urine collection system of the present invention having a positioning member 46, which can fit into the vaginal ostium and which also is attached to the conduit member 10. In contrast to the device as shown in FIG. 5, the positioning member in this embodiment is fabricated almost entirely of the sealing medium. With the exception of the area 48 surrounding the opening to conduit 10, the sealing medium is encompassed by a thin flexible layer of material 44.

Due to the excellent alignment of the conduit with the urethral ostium and its positioning in place by the sealing medium, the inner diameter of the conduit can be approximately equal to the diameter of the urethra itself. Exit drains employed in prior art devices are usually of a larger diameter than the urethral ostium since an alignment member is not employed and hence leakage can be a problem. A disadvantage of the prior art drains is that they tend to entrain, or entrap, air which makes disposal difficult in a gravity free environment such as might be encountered in outer space applications. Moreover, the larger diameter conduits take up unnecessary space for both storage and when in use.

In practice, it has been found that the diameter of the conduit or drainage tube should preferably be within the range of from about 3 to about 15 millimeters.

As hereinbefore indicated, the conduit which communicates between the urethral ostium and the urine collection and storage zone is sealably affixed to the tissue surrounding the ostium by a sealing medium. It is important that the sealing medium possess certain characteristics in order that it can be employed in the urine collection system of the present invention. The sealing medium must, of course, be inert to the tissue surrounding the urethral ostium and yet capable of forming a liquid tight seal so that all of the urine flows directly into the conduit.

Additionally, the sealing member must be capable of forming and maintaining a tight seal for extended periods of time and during times when the body may be in motion, and yet be capable of being detached from the body tissue without undue difficulty or discomfort. Hence, the sealing medium must be comprised of one or more materials which remain pliable, flexible and yet provide the necessary adhesive characteristic so that the urine collection system can be used with confidence.

It has been observed that a variety of materials can be used as a sealing medium of the present invention and which will not irritate the sensitive tissue surrounding the urethral ostium, and yet provide permanent tacky adhesion. May of the adhesive compositions presently on the market for use with ostomy appliances can be employed as long as they satisfy the aforementioned criteria. For example, compositions comprised of a hydrocolloid gum, a pressure sensitive adhesive and an agent which increases the cohesive strength of the composition, as described in U.S. Pat. No. 4,192,785 can be used as the sealing medium of the present invention. Other adhesive compositions which can be used are in the class of denture adhesives. Single-ingredient materials of interest are in the class of permanently tacky acrylic polymers.

Particularly preferred materials for use as the sealing medium in the urine collection system of the present invention are silicone gels. For example, it has been noted that cross linked polydimethylsiloxanes are soft, pliable, solid materials which possess a permanent tacky adhesiveness and are physiologicaly inert to the sensitive tissue surrounding the urethral ostium. These gels can be left in place for extended periods of time and yet readily pull free with little or no discomfort. Illustrative gels which are commercially available and useful in the urine collection system include, but are not limited to, Dow Corning's Q7-2218 gel and Petrarch System Inc's.

PEG-060. A variety of other gels can also be employed and will be readily apparent to those skilled in the art.

The support member, conduit or drainage tube, orientation member, can be fabricated from the same or different materials. A variety of thermoplastic materials, elastomeric materials, metals and the like, can be used in the fabrication of the system of this invention and such materials are known in the art.

As previously indicated, the urine collection system of the present invention is particularly attractive since it avoids or minimizes the infection problems associated with chronic or repeated catheterization. Since no invasion is made of the bladder through the urethra, direct transurethral transport of micro-organisms is avoided. However, to fully insure that any possible infection is avoided or minimized, the system of the present invention can also contain one or more antibacterial agents. For example, it has been observed that antibacterial agents can be incorporated directly into the sealing member used to affix the conduit to the tissue surrounding the urethral ostium. Antibacterial agents can also be incorporated into the polymeric material of which the supporting means conduit alignment member, or storage zone, are comprised.

Illustrative antibacterial agents which can be employed in the urine collection systems of the present invention include, among others, the metal salts of sulfonamides, such as silver sulfadizaine, thallium sulfadiazine, chlochexdine, neomycin, neomycin-polymixium mixture and the like.

The particular configuration of the urine collection system of the present invention will, of course, vary depending upon the need and physical condition or the user. For example, if the female using the device lacks the capability for physical movement and is, for instance, confined to a wheelchair or bed, conduit 10 may lead directly to a conventional toilet, or a bottle, bag, or similar collection vessel conveniently located near the patient. For an incontinent individual who is mobile, conduit 10 may lead to a flexible, expandable plastic bag which can be worn beneath the persons garments. The collection and storage zone can be maintained at a reduced pressure if desired. In many instances, the undergarments themselves will assist in holding the collection system in place.

The system of the present invention is also ideally suited for use by female astronauts who spend extended periods of time in a gravity free environment. The system can be entirely closed and due to the small diameter of the conduit or drainage tube, it can be compact in size and hence not interfere with the physical mobility of the user. Moreover, since the support member and conduit are affixed to the body tissue by the sealing medium, the system is leak-free and hence the astronaut's movement, while in a space ship or outside in a gravity-free environment, is not limited.

The device of the present invention is hence more compact than conventional female urine collection devices presently available and provides a freer way of life for the user. Moreover, since the system has no crevices or pockets where air might be entrapped, it is easily cleaned and may also be stored in antiseptic solutions.

Although the invention has been illustrated by the preceeding description, it is not to be construed as being limited to the materials employed therein, but rather, the invention encompasses the generic area as hereinbefore disclosed. Various modifications and embodiments can be made without departing from the spirit or scope thereof.

What is claimed is:

1. An enclosed, self-contained female urine collection system which can be worn for extended periods of time and which avoids the necessity for catheterization, whereby transurethral transport of micro-organisms are avoided, or minimized, said system comprised of in combination:
    (a) a flexible conduit for conducting urine from the urethral ostium to a urine collection and storage zone, said conduit having an internal diameter essentially the same as the urethra, and said conduit having disposed therein a movable, urethral positioning member whereby said conduit can be axially aligned with said urethral ostium,
    (b) a support member affixed to and circumferentially encompassing one end of said conduit and having disposed thereon a pliable, adhesive sealing medium whereby the lumen of said conduit can be sealably positioned in alignment with the ostium of said urethra using said urethral positioning member and whereby said conduit does not penetrate said urethra, but is maintained in a leak-free relationship therewith so that urine can flow from said urethral ostium through said conduit to said collection and storage zone, and
    (c) said urine collection and storage zone located at a point on said conduit distant from said urethral ostium.

2. The urine collection system of claim 1, wherein said positioning member is slidably mounted in said conduit and after aligning the lumen of said conduit with the ostium of the urethra and adhesively conforming said support member to said tissue, said positioning member can be removed from the system.

3. The urine collection system of claim 1, wherein said positioning member is slidably mounted in said conduit and forms an integral part of said system.

4. The urine collection system of claim 1, wherein said positioning member is cylindrical in shape and has a rounded end which engages the urethral ostium.

5. The urine collection system of claim 1 wherein said positioning member has an outer diameter of from about 2 to about 5 millimeters and said conduit has an internal diameter of from about 2.5 to about 10 millimeters.

6. The urine collection system of claim 1, wherein said positioning member is comprised of polytetrafluoroethylene.

7. The urine collection system of claim 1, wherein said sealing member is a gel.

8. The urine collection system of claim 7, wherein said gel has incorporated therein an anti-microbial agent.

9. The urine collection system of claim 8, wherein said anti-microbial agent is a silver salt of a sulfonamide.

10. The urine collection system of claim 8, wherein said anti-microbial agent is silver sulfadiazine.

11. The urine collection system of claim 1, wherein said sealing medium is a silicone gel.

12. The urine collection system of claim 1, wherein said conduit is comprised of an inert polymeric material.

13. The urine collection system of claim 12, wherein said polymeric material has incorporated therein an anti-microbial agent.

14. The urine collection system of claim 13, wherein said anti-microbial agent is a silver salt of a sulfonamide.

15. The urine collection system of claim 13, wherein said anti-microbial agent is silver sulfadiazine.

16. The urine collection system of claim 1, wherein said conduit contains a quick release connection disposed between said first end and said collection and storage zone.

17. The urine collection system of claim 1, wherein said collection and storage zone is under reduced pressure.

18. The urine collection system of claim 1, wherein said support member is shaped to conform to at least some portion of the female anatomy, in close proximity to the urethral ostium, so that said system is maintained in place during movement of the wearer.

19. The urine collection system of claim 18, wherein said support member is shaped so that said system is maintained in place by the labia minora and labia majora.

20. The urine collection system of claim 1 wherein said positioning member is substantially solid.

21. The urine collection system of claim 20 wherein said positioning member is comprised of an inert, polymeric material.

22. The urine collection system of claim 21, wherein said polymeric material has incorporated therein an anti-microbial agent.

23. The urine collection system of claim 22, wherein said anti-microbial agent is a silver salt of sulfonamide.

24. The urine collection system of claim 22, wherein said anti-microbial agent is silver sulfadiazine.

25. A positioning device suitable for alignment of the lumen of a conduit with the urethral ostium, said device comprised of a conduit having an internal diameter essentially the same as said urethral ostium, a support affixed to and circumferentially encompassing one end of said conduit and having disposed thereon a pliable, adhesive sealing medium whereby the lumen of said conduit can be sealably positioned in alignment with the ostium of said urthera and whereby said conduit does not penetate said urethra, but is maintained in a leak-free relationship therewith so that urine can flow from said urethral ostium through said conduit to a collection and storage zone, and a urethral positioning member slidably mounted in said conduit whereby the lumen of said conduit can be axially aligned with said urethral ostium.

* * * * *